(12) United States Patent
Periwal (10) Patent No.: US 7,512,497 B2
(45) Date of Patent: Mar. 31, 2009

(54) SYSTEMS AND METHODS FOR INFERRING BIOLOGICAL NETWORKS

(75) Inventor: Vipul Periwal, Bethesda, MD (US)

(73) Assignee: Gene Network Sciences, Inc., Cambridge, MA (US)

( * ) Notice: Subject to any disclaimer, the term of this patent is extended or adjusted under 35 U.S.C. 154(b) by 267 days.

(21) Appl. No.: 10/652,910

(22) Filed: Aug. 29, 2003
(Under 37 CFR 1.47)

(65) Prior Publication Data
US 2004/0243354 A1    Dec. 2, 2004

Related U.S. Application Data

(60) Provisional application No. 60/406,764, filed on Aug. 29, 2002.

(51) Int. Cl.
*G06F 1/00* (2006.01)
(52) U.S. Cl. .......................... 702/19; 702/20; 702/188; 703/11; 707/102
(58) Field of Classification Search .................. None
See application file for complete search history.

(56) References Cited

U.S. PATENT DOCUMENTS

| 5,980,096 | A | 11/1999 | Thalhammer-Reyero | |
|---|---|---|---|---|
| 6,051,029 | A | 4/2000 | Paterson et al. | |
| 6,132,969 | A | 10/2000 | Stoughton et al. | |
| 6,983,227 | B1 | 1/2003 | Thalhammer-Reyero | |
| 6,539,347 | B1 | 3/2003 | Paterson et al. | |
| 6,816,914 | B1 | 11/2004 | Heinzman et al. | |
| 2001/0023419 | A1 | 9/2001 | Lapointe et al. | |
| 2003/0097693 | A1* | 5/2003 | Morohashi et al. | 930/10 |
| 2003/0208284 | A1* | 11/2003 | Stewart et al. | 700/30 |

FOREIGN PATENT DOCUMENTS

| EP | 762294 | 3/1997 |
|---|---|---|
| EP | 1248231 | 10/2002 |
| WO | WO 01/48690 | 7/2001 |
| WO | WO01/48690 * | 7/2001 |
| WO | WO 03/042857 A1 | 5/2003 |
| WO | WO 03/063052 | 7/2003 |
| WO | WO 03/065244 | 8/2003 |

OTHER PUBLICATIONS

Steffen, M. Automated Modelling of singal transduction networks. BMC Bioinformatics 2002, 3:34.*
Bhan et al. Bioinformatics, vol. 18 (11) p. 1486-1493 Nov. 1, 2002.*
Gomez et al. Bioinformatics vol. 19 (15) 1875-1881, Oct. 12, 2003.*
Husmeier, D. Bioinformatics, vol. 19 (17) 2271-2282, Nov. 22, 2003.*
Bader, J. Bioinformatics, vol. 19 (15) 1869-1874, Oct. 12, 2003.*
Sveiczer, Aveiczer et al., Modeling the fission yeast cell cycle: Quantized cycle times in wee1⁻cdc25Δ mutant cells. PNAS 97: 14, 7865-7870 (Jul. 5, 2000).
Tomita et al, E-Cell: software environment for whole-cell simulation. Bioinformatics. 15: 1, 72-84 (1999).
Gomez et al., "Probabilistic Prediction of Unknown Metabolic and Signal-Transduction Networks", Genetics, vol. 159, pp. 1291-1298 (2001).
Akutsu et al., "Inferring qualitative relations in genetic networks and metabolic pathways", Bioinformatics, vol. 16, No. 8 2000, pp. 727-734 (2000).

* cited by examiner

*Primary Examiner*—Mary K Zeman
(74) *Attorney, Agent, or Firm*—Ropes & Gray LLP (57) ABSTRACT

Described herein is a system for inferring one or a population of biochemical interaction networks, including topology and chemical reaction rates and parameters, from dynamical or statical experimental data, with or without spatial localization information, and a database of possible interactions. Accordingly, the systems and methods described herein may be employed to infer the biochemical interaction networks that exist in a cell. To this end, the systems and methods described herein generate a plurality of possible candidate networks and then apply to these networks a forward simulation process to infer a network. Inferred networks may be analyzed via data fitting and other fitting criteria, to determine the likelihood that the network is correct. In this way, new and more complete models of cellular dynamics may be created.

11 Claims, 7 Drawing Sheets

SYSTEMS AND METHODS FOR INFERRING BIOLOGICAL NETWORKS

CROSS-REFERENCE TO RELATED APPLICATIONS

This application claims priority to Provisional U.S. patent application Ser. No. 60/406764, filed on Aug. 29, 2002, hereby incorporated herein by reference in its entirety.

BACKGROUND OF THE INVENTION

1. Field of the Invention

This invention relates to methods and systems inferring one or more biochemical interaction networks, including topology and chemical reaction rates and parameters, from experimental data and a database of possible interactions.

2. Description of the Related Art

Recent advances in bioinformatics have provided an extensive amount of statistical data on different aspects of cellular biology, including gene expression data. This statistical data has allowed for relocating the study of biology from a traditional laboratory setting involving test tubes and microscopes to a different kind of laboratory, consisting mainly of computer terminals. This new area of study is often referred to as in silico biology. A recent area of focus of in silico biology has been the development of computer models simulating and predicting genomic behavior, such as the study of drug targets for the remediation of a given disease condition. Previously, computer simulated biochemical network models were subject to constraints due to the limited availability of experimental data. However, recent developments in high-throughput methodologies able to rapidly amass large quantities of genomic data are making data constraints a problem of the past.

As increasing amounts of genomic-scale data becomes available, a new problem arises in trying to translate large stores of information into a useful, digestible form that enables accurate predictions of cell behavior. Currently, researchers must return to the lab each time they encounter an unknown variable, such as the presence or absence of a link in a particular disease pathway. This limits the efficiency of drug discovery, and requires researchers to make assumptions not accurately reflecting the complex nature of the biochemical interaction network underlying biological process. With in silico, or computer-simulated, biochemical interaction networks, a researcher may quickly predict the effects of unknowns on disease pathways and drug targets without leaving the comfort of their desks.

Unfortunately, the limited availability of genomic data was not the only constraint on the efforts to create accurate network models. Rather, a limited knowledge of the complex biochemical circuitry at the cellular level remains a real obstacle to the predictive accuracy of any in silico biological model. Thus, there exists a need for identifying, modeling or otherwise accounting for the manner in which cells operate.

SUMMARY

Described herein is a system for inferring one or a population of biochemical interaction networks that exist in a cell, including their topology and chemical reaction rates and parameters, from dynamic or static experimental data and a database of possible interactions. The systems and methods described herein generate a plurality of possible candidate networks from a seed pool of known or hypothesized networks, applies a forward simulation process to evaluate the fitness of the hypothesized networks and performs a global optimization (such as the well-known simulated annealing technique) to iteratively infer and test new networks.

Inferred networks may be analyzed via data fitting and other criteria to determine the likelihood that the network is correct, i.e., that it matches observed and/or hypothesized experimental data. In this way, new and more complete models of cellular dynamics may be created.

In some embodiments, filtering (or prescreening) may be performed on the set of generated networks to reduce the computational load on the simulation modules. Such filtering may include applying finite-state machine based comparisons with experimental data or other selection criteria to candidate networks.

BRIEF DESCRIPTION OF THE DRAWINGS

The present disclosure may be better understood and its numerous features and advantages made apparent to those skilled in the art by referencing the accompanying drawings.

FIGS. 6A and 6B show an example of the joint probability matrices measured on a synthetic test system. FIG. 6A is computed at a high annealing temperature; FIG. 6B is computed at a low annealing temperature.

The use of the same reference symbols in different drawings indicates similar or identical items.

DETAILED DESCRIPTION

Described herein is a system for inferring one or a population of biochemical interaction networks, including topology and chemical reaction rates and parameters, from dynamic or static experimental data, with or without spatial localization information, and a database of possible interactions. Accordingly, the systems and methods described herein may be used to infer the biochemical interaction networks that exist in a cell. To this end, the systems and methods described herein generate a plurality of possible candidate networks and then apply to these networks a forward simulation process to evaluate the fitness of the hypothesized networks and performs global optimization (such as the well-known simulated annealing technique) to infer a network. Inferred networks may be analyzed via data fitting and other criteria to determine the likelihood that the network is correct. In this way, new and more complete models of cellular dynamics may be created.

Figure 1:
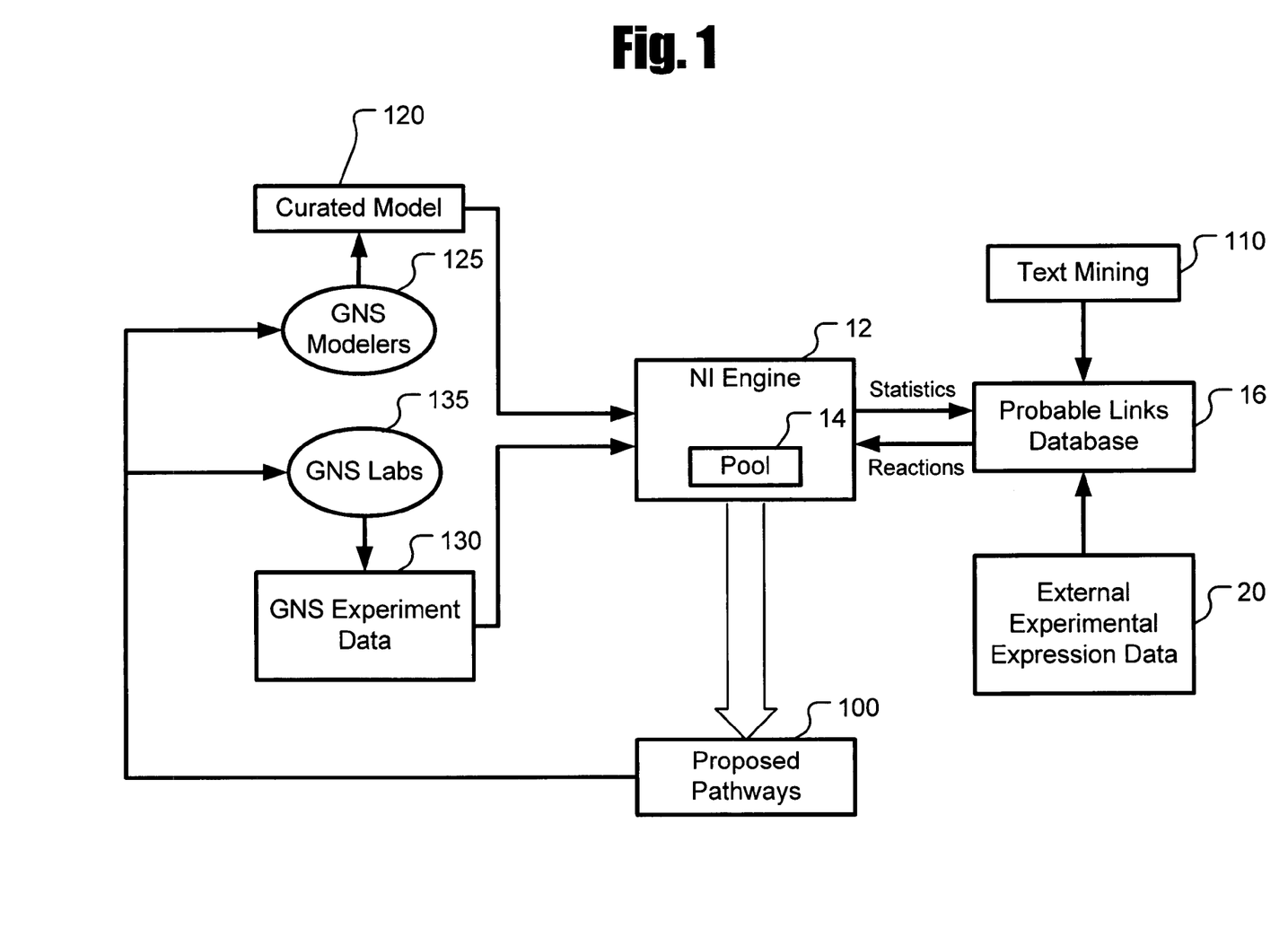
FIG. 1 depicts schematically a high-level representation of a process and system for inferring biological networks according to an exemplary embodiment of the invention.

FIG. 1 depicts a network inference (NI) engine 12 that creates new reaction network models by optimizing an evolving population (pool 14) of networks generated by addition (or deletion) of one or more network fragments (reactions operating on chemicals) drawn from a probable links database 16 to the pool 14. Each of these networks is comprised of the curated network 120 and one or more additional network fragments from the probable links database 16.

The initial pool of networks 14 is created by selecting network fragments from the probable links database 16 as directed by network generator 210 (further discussed with reference to FIG. 2) using the curated network as a seed network. In this way, the first generation of networks in the network pool 14 consists of combinations of the curated network 120 and one or more of the network fragments contained in the probable links database 16. The network pool 14 evolves through a series of iterations or generations where, through the course of each generation, each network in the pool is kept or replaced such that the net result is that the pool of networks grows closer to the biology of the target cell.

The network inference process starts from the curated model 120. The curated model is the current "best" approximation of a model of the biochemical reaction network representing a particular cell, such as a colon cancer cell. Although present examples of a curated network were created and are curated by hand, future curated models 120 may be developed and maintained (in some embodiments) with the aid of scientists from Gene Network Sciences, Inc. (GNS), i.e., the "GNS Modelers" 125. The model 120 itself is a list of reactions that act on a defined set of chemicals (e.g., genes, proteins or metabolites), i.e., the union of a list of network fragments. The model 120 may be represented in text form, as a simple (albeit long) list of reactions with chemicals with associated parameters (such as but not limited to concentration, rate, temperature, catalyst, etc. as are well-known in the art).

An example of the form of the text representation, using a conventional notation familiar to one of ordinary skill in the art, is as follows. The first characters in each reaction ("BUC" in the first reaction listed here) denote the reaction type. The terms inside the parenthesis and preceding the "|" character are the input and out put chemicals. The terms inside the parenthesis after the "|" are the parameters of the reaction.

```
BUC(casp8, Bid, casp8_Bid, tBid|kb_casp8_Bid, ku_casp8_Bid,
    kua_casp 8_Bid);
TR(tBid, tBidMito|kt_tBid_Mito);
BUC(tBid, BaxCyto, tBid_BaxCyto, Bax|kb_tBid_BaxCyto,
    ku_tBid_BaxCy to, kut_tBid_BaxCyto);
BU(tBidMito, Bax, tBid_Bax|kb_tBid_Bax, ku_tBid_Bax);
BU(tBid_Bax, Bax, tBid_Bax_Bax|kb_tBid_Bax, ku_tBid_Bax);
HDDR(tBid_Bax_Bax, tBidMito, Bax2|kua_tBid_Bax2);
BU(Bax, BclxL, Bax_BclxL|kb_Bax_BclxL, ku_Bax_BclxL);
BU(Bax, Bcl2, Bax_Bcl2|kb_Bax_Bcl2, ku_Bax_Bcl2);
BU(Bcl2, Bad, Bcl2_Bad|kb_Bcl2_Bad, ku_Bcl2_Bad);
BU(BclxL, Bad, BclxL_Bad|kb_BclxL_Bad, ku_BclxL_Bad);
BUC(p70S6KPhos, Bad, p70S6K_Bad, Bad1Phos|kb_p70S6K_Bad,
    ku_p70S6K_Bad, kua_p70S6K_Bad);
BUC(p70S6KPhos, Bad2Phos, p70S6K_Bad2Phos,
Bad1Phos2Phos|kb_p70S6K_
    Bad, ku_p70S6K_Bad, kua_p70S6K_Bad);
TR(Bad1Phos, Bad|kt_Bad_1Dephos);
TR(Bad1Phos2Phos, Bad2Phos|kt_Bad_1Dephos);
...
```

The model 120 may also be represented in the form of a bipartite graph with vertices denoting input (precursor) chemicals and reactions and illustrating resulting (output) chemicals. Furthermore, a pictorial or graphical representation may also be used. The model 120 may also be represented as ordinary differential equations, partial differential equations, Boolean switching networks, or stochastic differential equations. A sample portion of the curated network model 120 for a colon cancer cell in the form of differential equations is:

```
d[casp8]/dt      = – kb_casp8_Bid * [casp8] * [Bid] + ku_casp8_Bid * [casp8_Bid] +
    kua_casp8_Bid * [casp8_Bid] + kua_casp3_casp8i * [casp3_casp8i] – kb_casp8_casp3i
    * [casp8] * [casp3i] + ku_casp8_casp3i * [casp8_casp3i] + kua_casp8_casp3i *
    [casp8_casp3i]
d[Bid]/dt        = – kb_casp8_Bid * [casp8] * [Bid] + ku_casp8_Bid * [casp8_Bid]
d[casp8_Bid]/dt = kb_casp8_Bid * [casp8] * [Bid] – ku_casp8_Bid * [casp8_Bid] –
    kua_casp8_Bid * [casp8_Bid]
d[tBid]/dt       = kua_casp8_Bid * [casp8_Bid] – kt_tBid_Mito * [tBid] – kb_tBid_BaxCyto *
    [tBid] * [BaxCyto] + ku_tBid_BaxCyto * [tBid_BaxCyto] + kut_tBid_BaxCyto *
    [tBid_BaxCyto]
d[tBidMito]/dt   = kt_tBid_Mito * [tBid] – kb_tBid_Bax * [tBidMito] * [Bax] + ku_tBid_
    Bax * [tBid_Bax] + kua_tBid_Bax2 * [tBid_Bax_Bax]
d[BaxCyto]/dt    = –kb_tBid_BaxCyto * [tBid] * [BaxCyto] + ku_tBid_BaxCyto *
    [tBid_BaxCyto]
d[tBid_BaxCyto]/dt   = kb_tBid_BaxCyto * [tBid] * [BaxCyto] – ku_tBid_BaxCyto *
    [tBid_BaxCyto] – kut_tBid_BaxCyto * [tBid_BaxCyto]
d[Bax]/dt        = kut_tBid_BaxCyto * [tBid_BaxCyto] – kb_tBid_Bax * [tBidMito] * [Bax] +
    ku_tBid_Bax * [tBid_Bax] – kb_tBid_Bax * [tBid_Bax] * [Bax] + ku_tBid_Bax *
    [tBid_Bax_Bax] – kb_Bax_BclxL * [Bax] * [BclxL] + ku_Bax_BclxL * [Bax_BclxL] –
    kb_Bax_Bcl2 * [Bax] * [Bcl2] + ku_Bax_Bcl2 * [Bax_Bcl2]
d[tBid_Bax]/dt   = kb_tBid_Bax * [tBidMito] * [Bax] – ku_tBid_Bax * [tBid_Bax] –
    kb_tBid_Bax * [tBid_Bax] * [Bax] + ku_tBid_Bax * [tBid_Bax_Bax]
d[tBid_Bax_Bax]/dt = kb_tBid_Bax * [tBid_Bax] * [Bax] – ku_tBid_Bax * [tBid_Bax_
    Bax] – kua_tBid_Bax2 * [tBid_Bax_Bax]
d[Bax2]/dt       = kua_tBid_Bax2 * [tBid_Bax_Bax]
```

Figure 4:
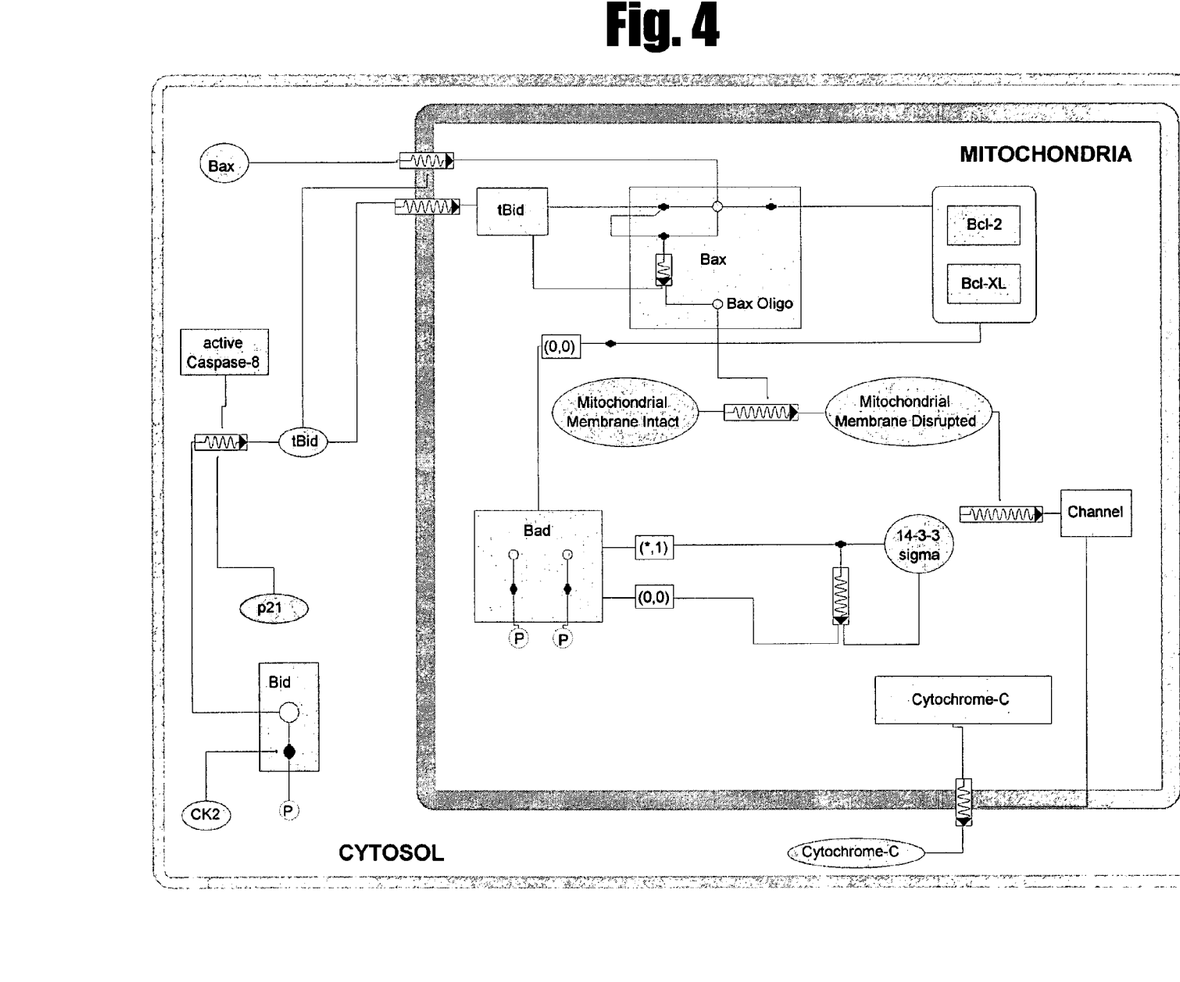
FIG. 4 is an example of a portion of a curated network displayed in graphical form, specifically using the Diagrammatic Cell Language.

FIG. 4 illustrates one exemplary curated model in Diagrammatic Cell Language form. This is the same model described above in the form of differential equations. Examples of other curated networks include the yeast cell cycle model described in Sveiczer, Á., Csikász-Nagy, A., Györffy, B., Tyson, J. J., Novák, B., "Modeling the fission yeast cell cycle: quantized cycle times in wee1⁻cdc25Δ mutant cells," Proc. Natl. Acad. Sci. USA, (2000), vol. 97, pp. 7865-7870, incorporated herein by reference in its entirety, and the MAP kinase cascade model described in Birgit Schoeberl, B., Eichler-Jonsson, C., Gilles, E. D., and Müller, G., "Computational modeling of the dynamics of the MAP kinase cascade activated by surface and internalized EGF receptors," Nature Biotechnology, Vol. 20, No. 4, pp. 370-375, incorporated herein by reference in its entirety.

In addition to the curated model 120, the network inference process also requires probable links database 16. Probable links database 16 consists of a library of possible network fragments (chemicals and reaction forms) that are candidates for addition to the curated network. Each network fragment is represented in the same form as the curated network—it is a collection of one or more reactions and chemicals inputs and outputs of those reactions. The probable links database also stores, for each network fragment, a prior estimated probability (based on confidences from text mining and other sources) that the network fragment is in the actual target biological network. In addition, probable links database 16 stores, for each pair of network fragments, an estimated joint probability that both network fragments are jointly in the actual target biological network.

Although an estimated joint probability is described, those skilled in the art will realize that joint probabilities for three or more networks could also be used. Accordingly, the invention is not limited to pair-wise joint probabilities.

Probable links database 16, generally, stores data representative of thousands of possible biochemical interactions that may occur in the cell of interest, as, for example, in the targeted colon cancer cell example discussed above. Each entry in the probable links database is collection of chemicals and connecting reactions (i.e., a network fragment) characterized by an estimated probability of the fragment being a part of the correct biology and a list of joint probabilities of inclusion along with the other entries in the probable links database. These network fragments may be obtained from bioinformatics predictions (e.g., via text mining 110 in FIG. 2) or by experimental data gathering 20, such as bio-assays of gene expression or other relevant data. These methods identify large numbers of candidate reactions—more than can practically be added by human hand to curated model 120. Moreover the number of networks that can be generated from all possible combinations of links (network fragments) in the database grows factorially with the number of links in the probable links database. Therefore, a brute-force computational evaluation of the fit to experiment of all possible networks is impractical.

Each form of the model is computer readable, i.e., it is in an electronic form accessible to and understandable by network engine 12. Thus, the computer-readable models are mathematical network representations of the biological processes within the cell. Inputs are in the form of computer-readable graphs that describe (1) the curated network; (2) the library of network fragments that comprise the probable links database; and (3) qualitative and quantitative data used as constraints on output from the curated network in combination with network fragments from the probable links database.

The network pool 14 stores previously inferred network models in one or more computer-readable forms, such as one or more databases, and provides seed network models to NI engine 12 for the creation of new network models at the start of each generation. At each iteration of global optimization, the NI engine 12 produces a new network pool that better fits the experimental data (i.e., it has a lower average cost) then the previous generation. The iteration is terminated by evaluating a conventional stopping criterion that measures the rate of improvement of the network pool. When this global optimization process has completed, the network pool consists of a many networks that well-match the experimental data (and other criteria incorporated into the fitness or cost function).

Network fragments that are common to many of these networks have high confidence of being part of the target cell's actual biological network. Thus, these proposed pathways 100 are candidates for inclusion in the curated network. In this way, the human modeler 125 may use the present invention to cull the factorially large number of candidate network fragments to a manageable number.

NI Engine 12 performs global optimization over the space of all networks that can be generated by combining the curated network 120 with all combinations of the entries in the probable links database 16 (not all possible networks are generated during the search). Well-known, conventional global optimization algorithms such as simulated annealing (described in, e.g., W. Gilks, S. Richardson and D. Spiegelhalter, *Markov Chain Monte Carlo in Practice*, Chapman and Hall, 1996, incorporated herein by reference in its entirety) or genetic algorithms (described in, e.g., D. E. Goldberg, *Genetic Algorithms in Search, Optimization & Machine Learning*, Addison-Wesley, 1989, incorporated herein by reference in its entirety) may be used to find the population of networks (which is the network pool 14) that best fits the experimental data (i.e., has the lowest cost).

Figure 5:
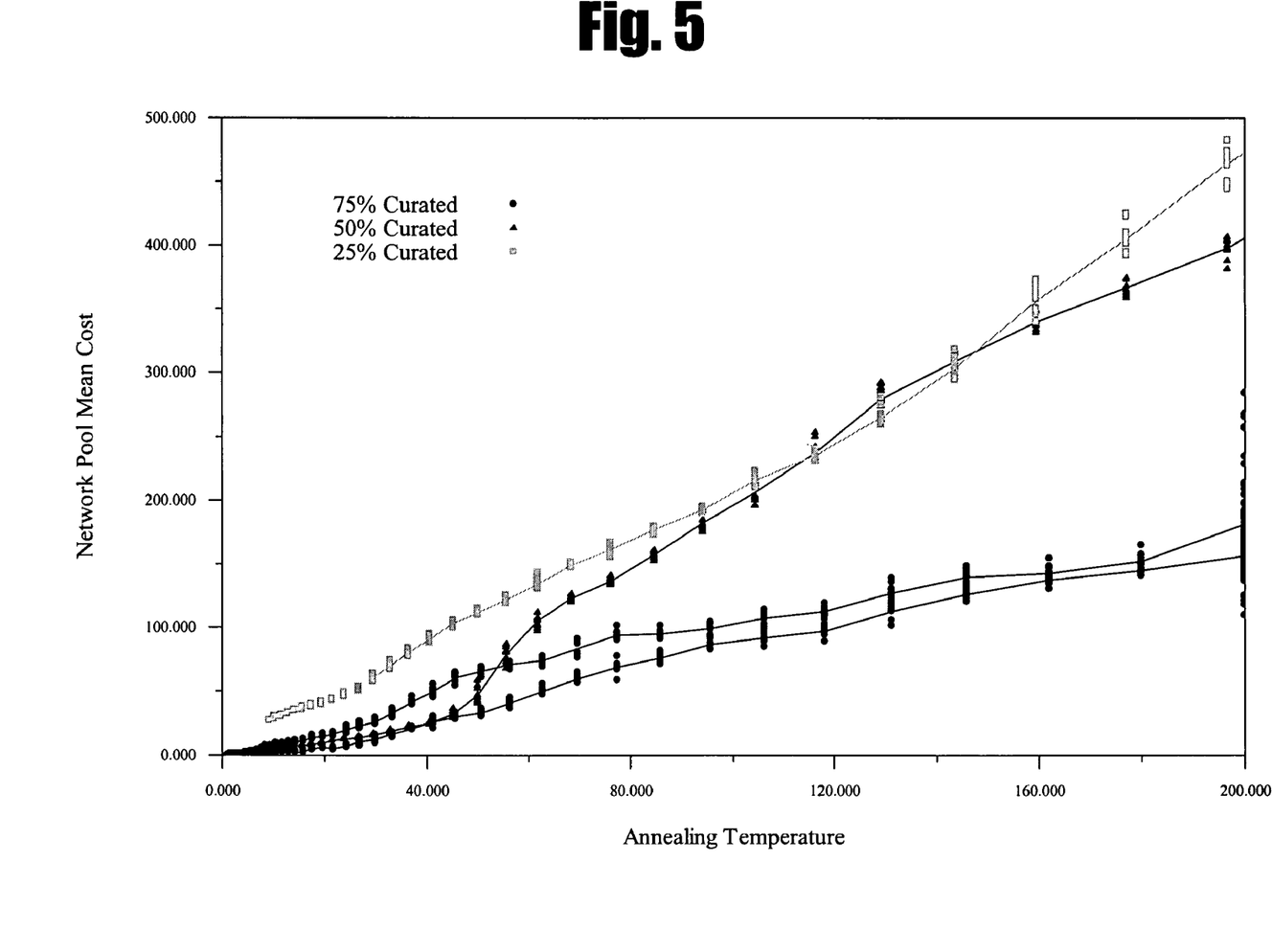
FIG. 5 is an example of the simulated annealing global optimization, showing the mean cost of all networks in an exemplary pool converging to zero (an exact match) as the annealing temperature is lowered

FIG. 5 illustrates an example of one type of global optimization protocol, conventionally referred to in the literature as simulated annealing. In a preferred embodiment of the present network inference engine, simulated annealing is employed for global optimization protocol. In the example shown in FIG. 5, the mean total cost for all networks in the network pool is displayed as a function of simulated annealing temperature for difference size curated networks relative to the complete network. These numerical experiments were performed on a model synthetic biology that consists of 25 chemical species interacting through bind and unbind reactions. A cost of zero is an exact match to the complete model network.

NI Engine 12 uses probable links database 16 to generate trial networks consistent with the probabilities and correlations stored in the probable links database.

Figure 2:
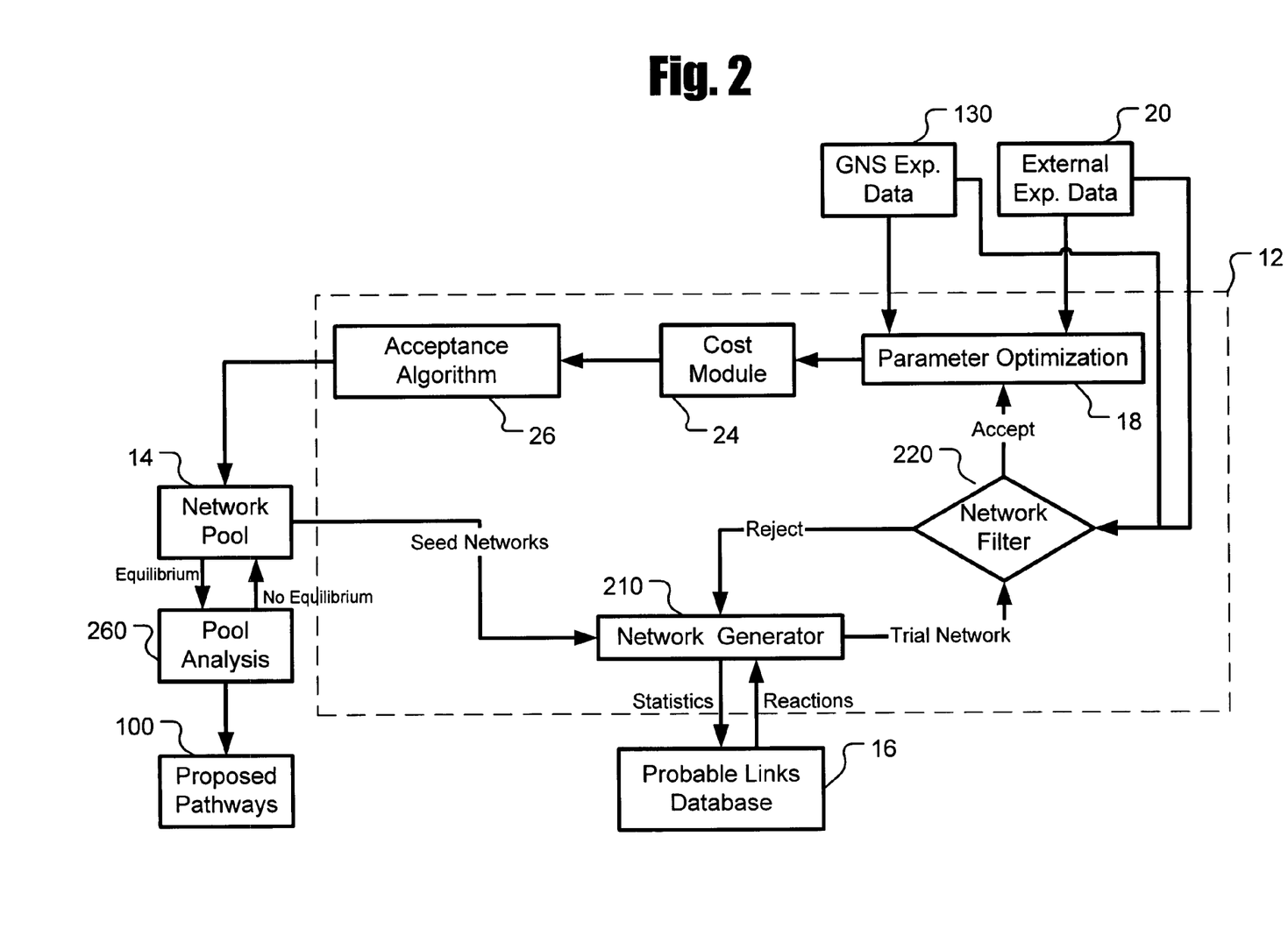
FIG. 2 depicts a high-level block diagram of a network inference engine according to one embodiment of the present invention.

FIG. 2 illustrates an exemplary embodiment of NI engine 12. For each generation of optimization, each network in the network pool 14 is used as a seed network by the network generator 210 to produce a trial network by adding to it or deleting from it one or more of the network fragments listed in the probable links database 16. In a genetic algorithm embodiment, the network generator may also generate new trial networks by recombination of more than one seed network, i.e., exchanging network fragments according to conventional genetic algorithm techniques well-known in the art. These trial networks may replace their source seed networks as described below.

Preferably, new trial networks are generated by a process of converting each seed network into a vector of spins s where the ith element of the vector is identified with the presence (s[i]=+1) or absence (s[i]=−1) of the network fragment with index i. The spin vector s is then the starting point for a stochastic Markov Chain process governed by a Hamiltonian H(s) that is a model that represents probability that a network fragment i is included as well as correlations between network fragments. For example $$H(s;h,k) = -\text{Log}[\text{Sum}[\text{Exp}[-s[i]*h[i]], i=1 \ldots N] + \text{Sum}[\text{Sum}[\text{Exp}[-s[i]s[j]k[i,j]], j=i+1 \ldots N], i=1 \ldots N]]$$

is a simple spin model where the vector h determines the probability that each spin is up (s=1) and the network fragment is included and conversely that each spin is down (s=−1) and the network fragment is excluded. Correlations between network fragments are determined by the off-diagonal elements of k.

The spin model incorporated in the preferred embodiment of network generator 210 improves the efficiency with which any of the global optimization strategies over the space of all possible networks (whether optimized by simulated annealing or with the use of a genetic algorithm) generate trial networks that differ by more than a single addition or deletion of a network fragment from the seed network yet have a greater likelihood of producing a good fit to experiment (also referred to herein as "valid" trial networks). This is because, on average, the generated networks have the same statistical properties (to first and second order) as the pool of networks that already have low cost (good fit) and/or the best prior estimates of the statistics from external experiment data.

The spin model parameters are determined from the first moment <s[i]> and second moment <s[i]* s[j]> of spins in the network pool and/or from the prior distributions stored in the probable links database. Given <s> and <s s>, h and k are determined by solving $$h = \text{Arc Sin } h[Z<s>/2^N]$$

$$k = \text{Arc Sin } h[Z<s\,s>2^N] \text{ and}$$

$$Z = 2^N(\text{Sum}[\text{Cos } h[h[i]], i=1\ldots N] + \text{Sum}[\text{Sum}[\text{Cos } h[k[i,j]], j=i+1\ldots N], i=1\ldots N])$$

The prior distribution (total and joint pairwise probabilities) stored in the probable links database may be used according to $$<s[i]> = 2*p[s[i]=1] − 1$$

and second moment:

$$<s[i]*s[j]> = p[s[i]=1\&s[j]=1] − p[s[i]=1\&s[j]=−1] − p[s[i]=−1\&s[j]=1] + p[s[i]=−1\&s[j]=−1]$$

Figure 6A:
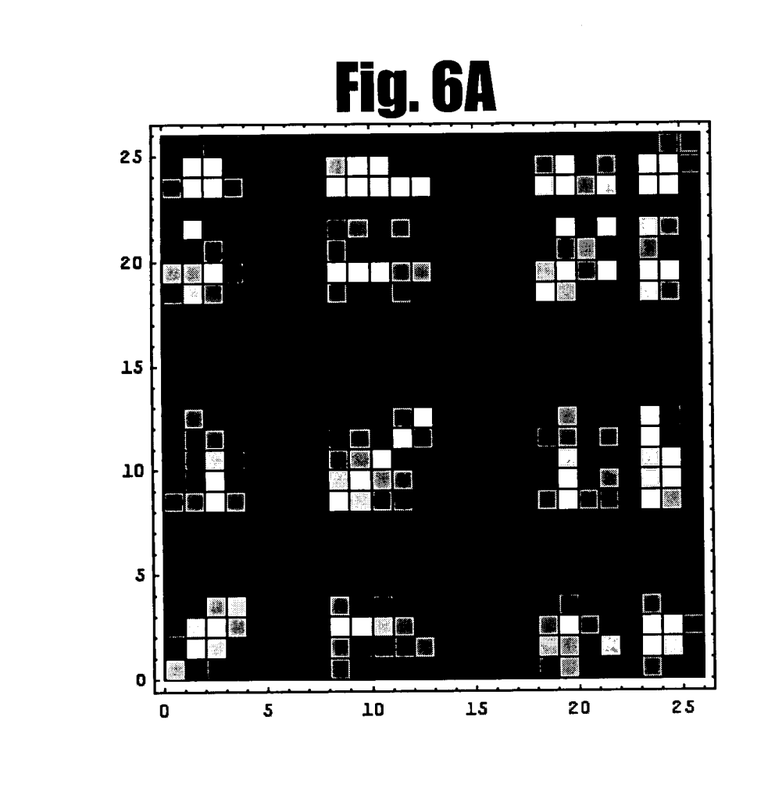
Figure 6B:
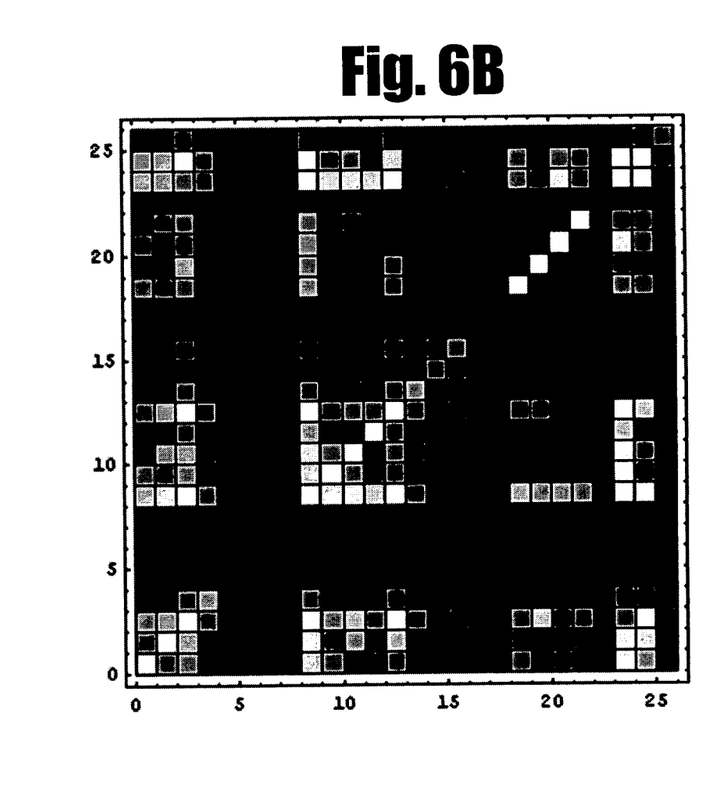

Examples of joint probability matrices measured on a synthetic test system with probable links database containing 26 network fragments (including the network fragments that make up the curated network) are shown in FIGS. 6A and 6B. The density plots show: (1) on the diagonal, the probability that the network fragment labeled by index is present in the network pool and (2) on the off diagonal, the value of joint probability for presence of both network fragments. White indicates high probability and black low. Each plot shows the probabilities at a different annealing temperature: FIG. 6A represents the probabilities at a high annealing temperature; FIG. 6B, at a low annealing temperature. While in this case the probabilities are observed from the network pool, the estimated prior (from text mining and external experimental data) total and prior joint probabilities stored in the probable links database have the same form and may be interpreted in the same manner.

FIG. 6 illustrates joint probability matrices measured on a synthetic test system with probable links database containing 26 network fragments. The x and y axis are the index of the network fragments.

Each candidate (trial) network passes through one or more network filters 220, which may comprise one or more discriminators that classify a proposed trial network pathway according to a pre-determined success or "goodness" criteria according to the networks topology without recourse to simulation of its biology. "Good" trial networks are referred to herein as valid trial networks; unsuitable trial networks are referred to as invalid. An example of such a technique is described in C. Conradi, et al., "Structure discrimination of continuous models for (bio)chemical reaction networks via finite state machines," *IEEE International Symposium on Intelligent Control* (2001), p. 138, incorporated herein by reference in its entirety.

The degree to which network is not scale-free may also be used to filter out networks based solely on their topology. Scale free networks are described, for example, in pending PCT application "Scale Free Network Inference Methods," application Ser. No. PCT/US02/35018, published on 22 May 2003 under publication no WO 03/042857, incorporated herein by reference in its entirety. In the present context, a scale-free trial network would be classified by the filtering step 220 as a valid trial network and passed on to parameter optimization 18.

Bayesian network belief propagation approximation methods for multiply connected networks (i.e. loopy belief propagation) may also be used to prescreen trial networks. See, e.g., J. Pearl, *Causality: Models, Reasoning and Inference*, Cambridge Univ. Press (2000), incorporated herein by reference in its entirety.

If the trial network is rejected by the network filter 220, the network generator 210 is reset to the same seed and a new trial network is generated. This filtering step 220 greatly improves computational efficiency by eliminating unlikely networks with the expensive step of parameter optimization described below.

As noted above, a spin model may be used to refine or filter the network reaction pathways produced by network generator 210. The spin model is a second-order model for the statistics of the reactions in network form, containing both the probability that a given pair of reactions is present and the correlation between the reactions. Although a simplified second-order model is described, one of ordinary skill in the art will recognize that the present invention is not so limited. Models of higher order, i.e., describing the probability of presence and correlation between three or more reactions are well-known in the art and computationally feasible, although expensive.

In creating the new network model, network generator 210 may draw one or more networks from the pool of existing networks 14 and incorporate one or any number of possible interactions from the probable links database 16.

Network generator 210 may also use the results of clustering large-scale or high-throughput experimental measurements 20 and/or 130, such as mRNA expression level measurements. (These experimental databases are also shown as an input to probable links database 16 and NI engine 12, respectively, in FIG. 1.) The results may also be combined with bioinformatics predictions such as for genes with common binding sites for transcription factors, or secondary structure predictions for proteins that may be possible transcription factors, to generate models consistent with these clustering and bioinformatics results, in combination or singly.

As will be understood by one of ordinary skill in the art, the systems and methods described herein allow for generating a population of networks and evaluating predictions from this population in a manner that is similar or equivalent to a Monte Carlo evaluation of the likelihood that the model is correct (in the Bayesian sense) over the ensemble of all networks weighted by the a priori measure of the space of networks.

Trial networks that pass through filter 220 may be sent to optional parameter optimization and simulation module 18, further described below with reference to FIG. 3. The parameter optimization and simulation module optimizes the fit simulation of the trial network with respect to the parameters of the reactions in the trial network while holding the topology of the trial network fixed. The output of this module is a best fit (lowest cost) to experimental data of the parameters for the trial network. This value is called the experimental cost.

Figure 3:
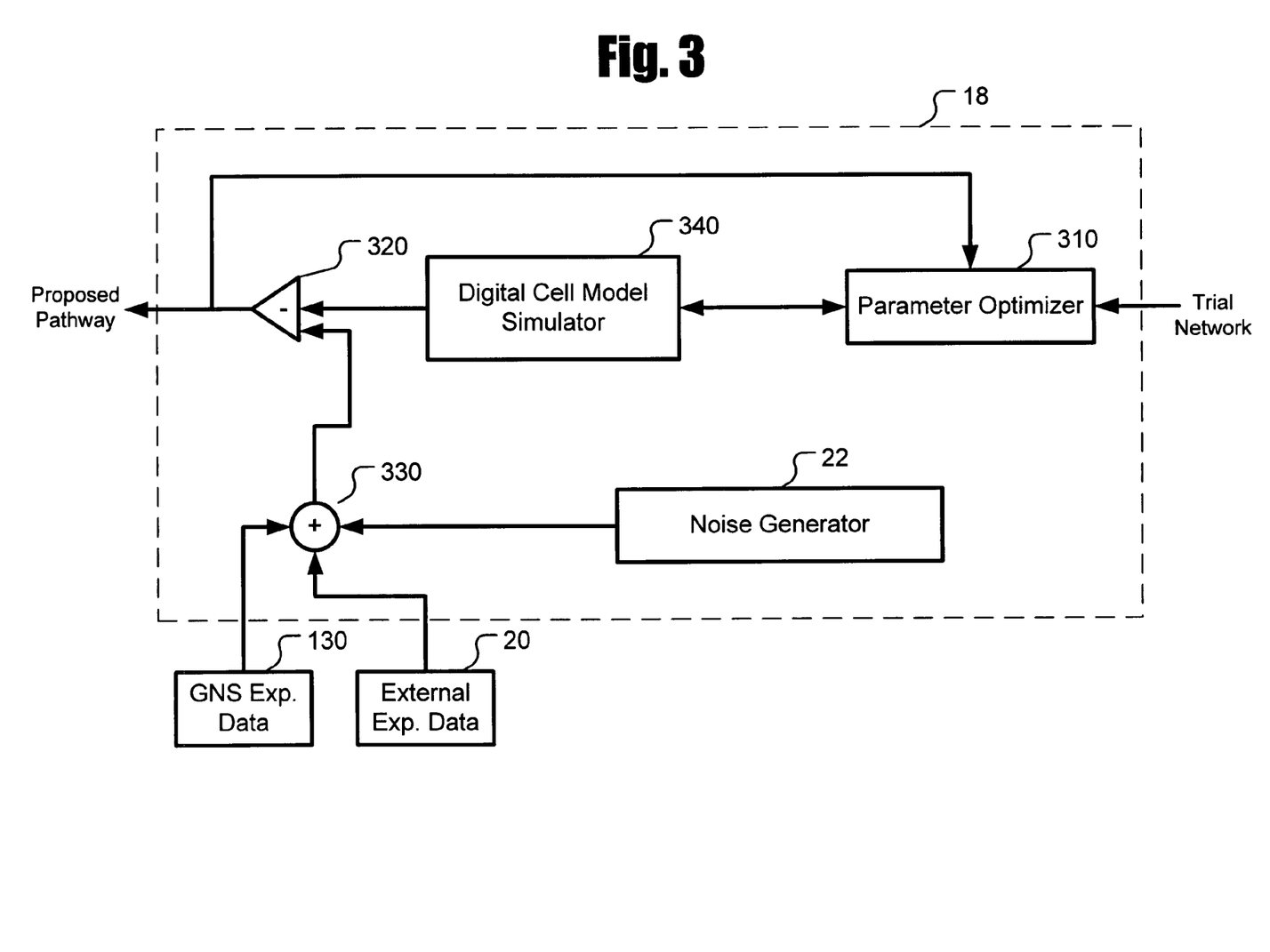
FIG. 3 depicts a high-level block diagram of the parameter optimization, simulation and comparison modules of the network inference engine according to one embodiment of the present invention.

FIG. 3 illustrates one exemplary embodiment of optional parameter optimization and simulation module 18 in further detail. Parameter optimization module 18 optimizes the model parameters received from the network generator 210 and network filter 220 using experimental data 20 and/or 130 as a calibration point, either in a single step or by coupling with a simulation module 340 for iterative parameter fitting. The optimization step tries to determine the rates of candidate reactions as well as the concentrations of the necessary precursor and resulting output chemicals, among other possible parameters for the reaction. Optimization may be accomplished using any global or local routine or combination of routines known to one of skill in the art. Examples include, but are not limited to, well-known local optimization routines such as Levenberg-Marquardt, modified Levenberg-Marquardt, BFGS-updated secant methods, sequential quadratic programming, or the Nelder-Mead method. Global optimization routines, such as simulated annealing or adaptive simulated annealing, basic Metropolis, genetic algorithms, and direct fitting may also be used.

An optional experimental noise generator 22 may also be used within or in conjunction with parameter-fitting module 18 to evaluate the model's sensitivity to fluctuations in the experimental data 20 and/or 130, i.e., to ensure that the results are robust to small changes in experimental data. The output of experimental noise generator 22 is summed 330 with experimental data 20 and/or 130. This summed data is then differentially combined 320 with the output of the parameter optimization 310/digital cell model simulation 340 process, thus introducing variations into the experimental data 20 (after parameter optimization) for evaluation by cost-evaluation module 24 (FIG. 2). Noise generation may be implemented by modeling the uncertainty in any given experimental observation by an appropriate distribution (e.g. log-normal for expression data) and picking noise values as dictated by the distribution for that experimental observation.

Figure 7:
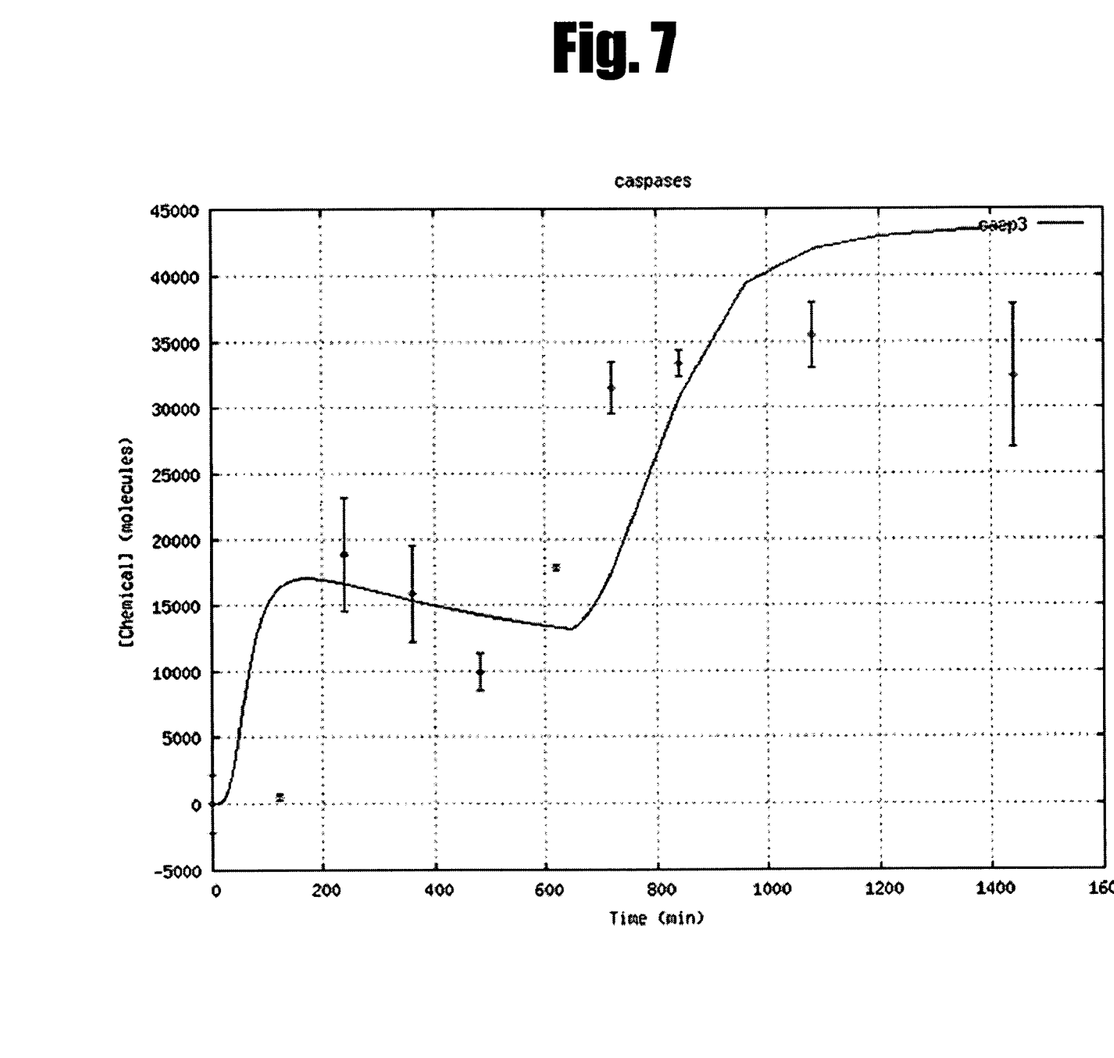
FIG. 7 is a comparison of the forward time simulation of a trial network with experimental data.

FIG. 7 shows a comparison of the forward time simulation of a trial network with experimental data for the same cell. In this exemplary experiment, the concentrations of the chemical Caspase-3 (one of many experimental constraints) were measured in the GNS Lab at specific time points over the course of 1600 minutes. Each data point from the experiment was also characterized by an uncertainty indicated by the error bars. The forward simulation of the trial network predicts the time course for Caspase-3 is plotted as the solid line. The experimental cost is a measure of the differences between the data and the model prediction. The parameter optimization module selects the model parameters (given the trial network) to best match the experimental data (i.e., resulting in the minimum cost).

Each resulting completed network is evaluated for cost by cost module 24 and sent to acceptance algorithm module 26. Cost module 24 may also test the reliability of the model and parameters by examining global and local fitness criteria.

Cost mixing module 24 combines the experimental cost (goodness of fit to experiment) calculated by the parameter optimization and module simulation module 18 with other costs that may include, but are not limited to: (1) insensitivity of the model to changes in the initial conditions or chemical reaction parameters; (2) robustness of the model to the random removal or addition of biochemical interactions in the network; (3) insensitivity to variations in the experimental data [with variations introduced into the experimental data in the experimental noise data 22]; and/or (4) overall bioinformatics costs associated with the model. Examples of well-known bioinformatics cost algorithms understood by those of ordinary skill in the art are the number of gene prediction algorithms that simultaneously agree on a particular gene and the number of secondary structure prediction algorithms that agree on the structure of a protein. Some embodiments may also use other bioinformatics cost algorithms that allow comparison to synthetically generated sequence (or other) data, thereby allowing the calculation of likelihoods or confidence measures in the validity of a given prediction. Cost mixing module 24 outputs a single cost—the "total cost" for the trial network—along with a vector of the component costs for the trial network.

Acceptance algorithm 26 determines whether or not to replace the seed network with the trial network in the network pool based on the total costs of the seed and trial networks as well as their cost vectors. When, for example, using simulated annealing as the global optimization algorithm, the acceptance criteria (for replacing the seed network with the trial network) is

---

If ( TotalCost_trial < TotalCost_seed || TotalCost_trial −
TotalCost_seed < − T
   Log[Random(0,1)] )
   Then replace seed with trial
   Else discard trial

--- where T is the annealing temperature and Random(0, 1) generates random numbers with uniform distribution between 0 and 1.

Digital cell model simulator 340 is a set of differential equations that are run to see if, over time, the concentration of a particular chemical is increasing or decreasing in accordance with measured experimental data 20 or 130.

Alternate Embodiments

Experimental data 20 consists of qualitative or quantitative experimental data, such as MRNA or protein levels, stored in a computer database. Experimental data 20 may be obtained through any of a variety of high-throughput data collection techniques known to one of skill in the art, including but not limited to immunoprecipitation assays, Western blots or other assays, and gene expression from RT-PCR or oligonucleotide and cDNA microarrays. Experimental data 20 may be coupled directly with parameter optimization module 18 and optionally with experimental noise generator 22.

In an alternate embodiment, the systems and methods described herein may employ other types of data, including, for example, spatial localization data. Preferably, the model has (x, y, z, t) spatial and temporal coordinates for components as well. Confocal microscopy, by way of example and not of limitation, is one of the technologies for getting both spatial and dynamic (temporal) localization. One example of why this is important is that the total levels of protein A may not change at all as a result of a perturbation, but its level in the cytosol versus nucleus may be changing as a result of the perturbation, whereby A is getting translocated from cytosol to nucleus to participate in other processes. In some embodiments, the present system and methods may use both dynamic and static data as well as information on spatial localization.

In another alternate embodiment, models in the population of existing networks may continue to be evaluated and tested by adding and removing links (pathways) in an iterative operation of the system herein described. Users of the system may generate networks entirely from the probable links database 16, or from a combination of the probable links database 16 with the population of existing networks 14. Iterative refinement may continue until a single network attains a desired goodness of fit to experimental data, perhaps combined with low (e.g., below a user-defined threshold) costs for dynamic robustness or other criteria, or until a stable, dynamically-similar cluster of networks emerges from the population of networks. This stable cluster may then be used to compute robust predictions by averaging over the predictions of elements of the cluster of networks, in a cost-weighted average, where the costs include, but are not limited to, goodness of fit to the experimental data, dynamic robustness, probabilistic or exact evaluation of insensitivity to experimental noise and/or parameter values. Thus, networks with lower costs may contribute more to predictions than networks with higher costs. The refinement of the pool of networks may be continued until the (average or best) goodness of fit of the networks in the stable cluster is below some user defined threshold, or until the number of networks in the cluster is above some user defined threshold. In the case of the single network that may be the result of the inference process, the single network may be solely used for generating predictions.

The process described herein may be executed on a conventional data processing platform such as an IBM PC-compatible computer running the Windows operating systems, a SUN workstation running a UNIX operating system or another equivalent personal computer or workstation. Alternatively, the data processing system may comprise a dedicated processing system that includes an embedded programmable data processing unit. For example, the data processing system may comprise a single board computer system that has been integrated into a system for performing micro-array analysis.

The process described herein may also be realized as a software component operating on a conventional data processing system such as a UNIX workstation. In such an embodiment, the process may be implemented as a computer program written in any of several languages well-known to those of ordinary skill in the art, such as (but not limited to) C, C++, FORTRAN, Java or BASIC. The process may also be executed on commonly available clusters of processors, such as Western Scientific Linux clusters, which are able to allow parallel execution of all or some of the steps in the present process.

Accordingly, the systems and methods described herein include systems that create a pool of candidate or possible networks that have been generated to match data, including data that is biologically realistic (as defined or explicated in relevant literature or experiments). The systems described herein may, in certain embodiments, apply a discriminator process to the generated pool of possible networks. In an iterative process, the system may employ pools identified by the discriminator process as data that may be applied to a network generation module. The network generation module may then process these possible networks with data from the probable links database to generate output data that can be processed by the fitting module as described above. In this way, the systems and methods described herein may derive predictions from a pool of networks, instead of processing biological data to generate a single unique network.

As noted above, the order in which the steps of the present method are performed is purely illustrative in nature. In fact, the steps can be performed in any order or in parallel, unless otherwise indicated by the present disclosure.

The method of the present invention may be performed in either hardware, software, or any combination thereof, as those terms are currently known in the art. In particular, the present method may be carried out by software, firmware, or microcode operating on a computer or computers of any type. Additionally, software embodying the present invention may comprise computer instructions in any form (e.g., source code, object code, interpreted code, etc.) stored in any computer-readable medium (e.g., ROM, RAM, magnetic media, punched tape or card, compact disc (CD) in any form, DVD, etc.). Furthermore, such software may also be in the form of a computer data signal embodied in a carrier wave, such as that found within the well-known Web pages transferred among devices connected to the Internet. Accordingly, the present invention is not limited to any particular platform, unless specifically stated otherwise in the present disclosure.

While particular embodiments of the present invention have been shown and described, it will be apparent to those skilled in the art that changes and modifications may be made without departing from this invention in its broader aspect and, therefore, the appended claims are to encompass within their scope all such changes and modifications as fall within the true spirit of this invention. Furthermore, those skilled in the art will know or be able to ascertain (using no more than routine experimentation) many equivalents to the embodiments and practices described herein. Accordingly, it will be understood that the invention is not to be limited to the embodiments disclosed herein, but is to be interpreted as broadly as allowed under the law.

I claim:

1. A method of inferring cellular structural networks, comprising:
   (a) furnishing to a first physical computing device a seed network comprising a plurality of links;
   (b) using the first physical computing device, iteratively:
      (b1) generating a trial network by combining one or more probable links selected from a probable links database with said seed network;
      (b2) filtering each said trial network according to its topology to determine if said trial network is an invalid trial network; and
      (b3) repeating steps (b1) through (b2) until said filtering determines said trial network is a valid trial network;
   (c) using the first physical computing device or a second physical computing device, determining a cost for each said valid trial network;
   (d) using the first physical computing device or a second physical computing device, accepting or rejecting said valid trial network for inclusion in a pool of networks based on said cost;
   (e) repeating steps (b) through (d) until a selected number of links in said probable links database have been combined into trial networks;
   (f) repeating steps (a) through (e) until the average cost of said valid trial networks in said pool reaches equilibrium to form a final pool;
   (g) using the first physical computing device or a second physical computing device, selecting one or more valid trial networks from said final pool having low cost; and
   (h) outputting through a display device or a communication device the one or more valid trial networks to a user, the one or more valid trial networks configured for simulating a biological structural network on a computer and predicting a behavior of the biological structural network.

2. The method of claim 1, wherein said generating a trial network further comprises employing a spin model.

3. The method of claim 1, wherein said filtering each said trial network further comprises determining if each said trial network is scale free.

4. The method of claim 1, further comprising:
(i) before step (c), using the first physical computing device, iteratively optimizing said valid trial network, said optimizing comprising
   (i1) postulating one or more parameter values for each link in said valid trial network;
   (i2) simulating said valid trial network with said postulated parameter values;
   (i3) comparing the results of said simulating with pre-existing data, said pre-existing data comprising experimental data;
   (i4) adjusting said postulated parameter values according to the results of said comparing; and
   (i5) repeating steps (i1) through (i4) until said comparing converges;
wherein said determining a cost for each said valid trial network is based at least in part on said optimizing.

5. The method of claim 4, wherein said comparing the results of said simulating with said data further comprises adding noise to said data prior to said comparing.

6. The method of claim 1, wherein said accepting or rejecting said valid trial network further comprises means for identifying and removing a valid trial network already in said pool.

7. The method of claim 6, wherein said means for identifying and removing a valid trial network comprise a simulated annealing protocol.

8. The method of claim 6, wherein said means for identifying and removing a valid trial network comprise a genetic algorithm.

9. The method of claim 1, wherein said selecting further comprises analyzing said valid trial networks in said final pool to identify one or more pathways common to a plurality of valid trial networks.

10. A system for inferring cellular networks, comprising:
(a) means for furnishing a seed network comprising a plurality of links;
(b) processing means for iteratively:
   (b1) generating a trial network by combining one or more probable links selected from a probable links database with said seed network;
   (b2) filtering each said trial network according to its topology to determine if said trial network is an invalid trial network; and
   (b3) repeating steps (b1) through (b2) until said filtering determines said trial network is a valid trial network;
(c) processing means for determining a cost for each said valid trial network;
(d) processing means for accepting or rejecting said valid trial network for inclusion in a pool of networks based on said cost;
(e) repeating steps (b) through (d) until a selected number of links in said probable links database have been combined into trial networks;
(f) repeating steps (a) through (e) until the average cost of said valid trial networks in said pool reaches equilibrium to form a final pool;
(g) processing means for selecting one or more valid trial networks from said final pool having low cost; and
(h) displaying means for outputting the one or more valid trial networks to a user, the one or more valid trial networks configured for simulating a biological network on a computer and predicting a behavior of the biological network.

11. A computer system for use in inferring cellular networks, comprising:
a computer comprising one or more processors, a display device, and a memory device, the one or more processors configured for:
(a) furnishing a seed network comprising a plurality of links;
(b) iteratively:
   (b1) generating a trial network by combining one or more probable links selected from a probable links database with said seed network;
   (b2) filtering each said trial network according to its topology to determine if said trial network is an invalid trial network; and
   (b3) repeating steps (b1) through (b2) until said filtering determines said trial network is a valid trial network;
(c) determining a cost for each said valid trial network;
(d) accepting or rejecting said valid trial network for inclusion in a pool of networks based on said cost;
(e) repeating steps (b) through (d) until a selected number of links in said probable links database have been combined into trial networks;
(f) repeating steps (a) through (e) until the average cost of said valid trial networks in said pool reaches equilibrium to form a final pool;
(g) selecting one or more valid trial networks from said final pool having low cost; and
(h) outputting to the display device, the one or more valid trial networks to a user, the one or more valid trial networks configured for simulating a biological network on a computer and predicting a behavior of the biological network.

* * * * *